(12) United States Patent
Speer et al.

(10) Patent No.: US 11,123,777 B2
(45) Date of Patent: Sep. 21, 2021

(54) SYSTEM AND METHODS FOR MONITORING AND CONTROLLING AN AEROBIC LANDFILL BIOREACTOR

(71) Applicant: AEROBIC LANDFILL TECHNOLOGIES INC., London (CA)

(72) Inventors: Sean Speer, Calgary (CA); Leon Green, Aiken, SC (US)

(73) Assignee: Aerobic Landfill Technologies Inc., London (CA)

( * ) Notice: Subject to any disclaimer, the term of this patent is extended or adjusted under 35 U.S.C. 154(b) by 0 days.

(21) Appl. No.: 16/262,553

(22) Filed: Jan. 30, 2019

(65) Prior Publication Data

US 2019/0232346 A1 Aug. 1, 2019

Related U.S. Application Data

(60) Provisional application No. 62/624,442, filed on Jan. 31, 2018.

(51) Int. Cl.
| | |
|---|---|
| *B09B 1/00* | (2006.01) |
| *E21B 49/08* | (2006.01) |
| *C12M 1/34* | (2006.01) |
| *E21B 33/068* | (2006.01) |

(Continued)

(52) U.S. Cl.
CPC ............. *B09B 1/006* (2013.01); *C12M 41/34* (2013.01); *C12M 41/48* (2013.01); *E21B 33/068* (2013.01); *E21B 34/02* (2013.01); *E21B 49/08* (2013.01)

(58) Field of Classification Search
CPC ...................................................... B09B 1/006
See application file for complete search history.

(56) References Cited

U.S. PATENT DOCUMENTS

| | | | | |
|---|---|---|---|---|
| 2006/0222464 | A1* | 10/2006 | Schwalbe | B09B 1/006 405/129.95 |
| 2008/0127726 | A1* | 6/2008 | Elkins | E21B 47/00 73/152.42 |

(Continued)

*Primary Examiner* — Janine M Kreck
(74) *Attorney, Agent, or Firm* — McMillan LLP

(57) ABSTRACT

A system and method for monitoring or controlling an aerobic landfill bioreactor having a plurality of zones each including at least one well head. The system comprises: a gas extraction blower, a plurality of temperature sensors disposed in the well heads, an ex-situ relative humidity detector, an ex-situ gas constituent detector, an air injection system, a liquid injection system, and a controller. Landfill gas is extracted by the blower and it's temperature, relative humidity, and gas constituents are measured. The system further comprises a system of headers, isolation valves, and flow control valves which serve to isolate zones for measurement and/or air and liquid injection as well as control the flow of either the landfill gas extraction or liquid and air injection. The method involves measuring: temperature, relative humidity, and gas constituents of the extracted landfill gas. Advantageously, the ex-site placement of the sensors and detectors ensure that measurements are representative of the aerobic bioreactor operating parameters. The air and liquid injection systems are adjusted, based on the measured temperature, relative humidity, and gas constituents to optimize the operation of the aerobic landfill bioreactor.

20 Claims, 12 Drawing Sheets

(51) Int. Cl.
*C12M 1/36* (2006.01)
*E21B 34/02* (2006.01)

(56) References Cited

U.S. PATENT DOCUMENTS

2010/0032371 A1* 2/2010 Bentley .................. C02F 11/02
                                                          210/604
2017/0218730 A1* 8/2017 Campanella ............ E21B 43/00

* cited by examiner

SYSTEM AND METHODS FOR MONITORING AND CONTROLLING AN AEROBIC LANDFILL BIOREACTOR

RELATED APPLICATIONS

This application claims priority to U.S. Provisional Application Ser. No. 62/624,442, filed Jan. 31, 2018, entitled "System And Method For The Measurement Of Landfill Gas Characteristics," which is hereby incorporated by reference in its entirety.

FIELD OF THE INVENTION

This invention relates generally to aerobic landfill bioreactors, and more specifically to a system and methods for monitoring and controlling an aerobic landfill bioreactor.

BACKGROUND OF THE INVENTION

Landfills are large volume waste storage systems that allow for biological degradation of the labile organic fraction of the stored waste. Conventional landfilling practices involve the waste being applied into the cells, followed by compaction, and eventually closing the landfill with an impermeable cap to minimize moisture infiltration and therefore leachate production. The majority of the degradation of the waste occurs under anaerobic conditions, leading to hazardous and odorous gaseous by-products including: hydrogen sulphide, ammonia gas and methane. The leachate produced under these anaerobic conditions is typically a high strength wastewater characterized by a low pH and high concentrations of metals and xenobiotic compounds. Organic waste degradation in a conventional anaerobic landfill can take over 150 years to reach completion. Converting the conventional, anaerobic, landfill to an aerobic landfill bioreactor will decrease waste stabilization times, cease the production of methane, ammonia gas and hydrogen sulphide while also eliminating leachate production. Converting a conventional anaerobic landfill into an aerobic landfill bioreactor can decrease the waste stabilization time from over 150 years down to 5 years. Maintaining proper conditions within the stored waste is key to optimizing aerobic operations within the aerobic landfill bioreactor.

There are three main conditions within the stored waste that control the growth and activity rates of the aerobic heterotrophic microorganisms in an aerobic landfill bioreactor: temperature, moisture content, and available oxygen. There are only two inputs to the bioreactor system: air, and liquid. The two inputs can be modified to maintain the aforementioned three conditions (temperature, moisture, and oxygen) in optimal ranges.

Systems and methods exist for optimizing the aerobic degradation of organic material in landfills. There are two potential goals for the aerobic degradation of organic waste: to avoid methane production, or to minimize or eliminate leachate production. Two operating strategies also exist for the introduction of oxygen and/or moisture into the landfills for aerobic degradation. One method utilizes pipes to introduce air, or other oxygen-rich gases, and moisture to the landfill. Such methods may or may not include the collection of landfill gases. The other method utilizes oxygen-enriched liquids to act as both an oxygen and a moisture source.

Prior art references suggest the use of in situ monitoring equipment for temperature, moisture content, and oxygen content as a method of monitoring system efficiency. This involves the installation of multiple sensors throughout the landfill site. There are many problems associated with the use of in-situ sensors. Drilling in landfills is difficult due to the heterogeneous nature of the material. The difficulty of drilling is accompanied by an increased price, and longer timelines for drilling activities. The environment in the landfill can also be hazardous to the monitoring equipment, especially in the acidic and reducing environment present while the landfill is experiencing anaerobic degradation. The installation of these in-situ sensors is, therefore, both difficult and costly and the conditions within the landfill can be damaging to the equipment, requiring regular, costly, equipment replacement. The monitoring equipment is only capable of reading conditions in the vicinity of the sensors, which does not provide an accurate amalgam measurement for the whole landfill, and will likely not be accurate even for small areas of the landfill. The heterogeneity of the landfill leads to conditions within the landfill not being correctly measured through the use of in situ sensors. Without proper monitoring of these conditions in the landfill, aerobic landfill bioreactors cannot be operated with optimal efficiency, further increasing the cost of system operation, and the timeline for stabilization of the waste.

There is a need for better systems and methods for monitoring and controlling the operation of aerobic landfill bioreactors, which overcome at least some of the above-identified issues.

BRIEF DESCRIPTION OF THE DRAWINGS

Embodiments of the present invention will be presented below, with reference to the attached drawings, in which.

SUMMARY OF THE INVENTION

Figure 1A:
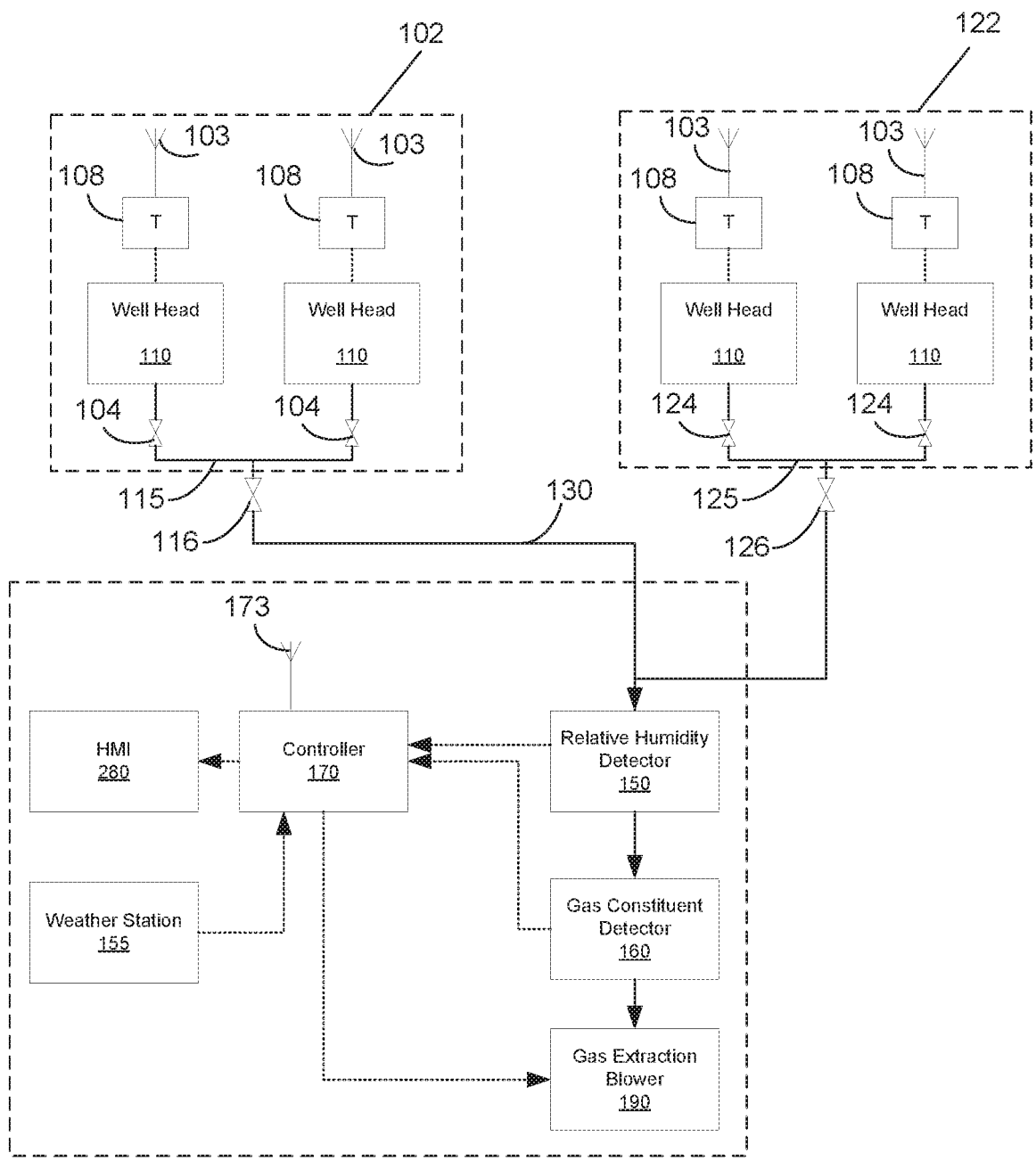
FIG. 1A is a block diagram of a system for monitoring and controlling the operation of an aerobic landfill bioreactor, in accordance with an embodiment of the present invention.

In one aspect of the present invention there is provided system for monitoring or controlling an aerobic landfill bioreactor having at least one gas extraction well head. The system comprises: a gas extraction system, a temperature sensor, and a controller. The gas extraction system is for extracting landfill gas from the aerobic landfill bioreactor, and includes: a gas extraction blower configured to draw landfill gas out of the aerobic landfill bioreactor via the at least one gas extraction well head; a relative humidity detector configured to measure a relative humidity in the extracted landfill gas; and a gas constituent detector configured to detect at least one gas constituent of the extracted landfill gas. The temperature sensor is disposed in the at least one gas extraction well head for measuring a temperature of the extracted landfill gas. The controller is configured for: receiving the measured temperature from the temperature sensor, receiving the measured relative humidity from the relative humidity detector, receiving the detected at least one gas constituent from the gas constituent detector, and controlling the gas extraction blower.

In one embodiment, at least one of: the relative humidity detector and the gas constituent detector is disposed in the gas extraction well head.

In one embodiment, the at least one gas extraction well head includes a flow control valve for controlling the extraction rate of landfill gas from the gas extraction well head.

In one embodiment, the system for controlling or monitoring an aerobic landfill bioreactor further comprises a precipitation measurement means for estimating the amount of liquid infiltrating into the aerobic landfill bioreactor. The precipitation measurement means may be coupled to the controller for providing precipitation measurements thereto.

In one embodiment, the aerobic landfill bioreactor comprises a plurality of zones. The at least one gas extraction well head comprises a plurality of gas extraction well heads with at least one gas extraction well head in each of the plurality of zones. The at least one flow control valve comprises a plurality of flow control valves configured for controlling the flow of the extracted landfill gas out of the plurality of gas extraction well heads. The gas extraction system further comprises a gas extraction zone header including a plurality of isolation valves configured for isolating at least one of the plurality of zones.

In one embodiment, the system for monitoring or controlling an aerobic landfill bioreactor further comprises an extraction zone valve controller.

In one embodiment, the extraction zone valve controller is operatively connected to the plurality of isolation valves, wherein isolating at least one of the plurality of zones comprises activating or deactivating at least one of the plurality of isolation valves by the extraction zone valve controller.

In one embodiment, the extraction zone valve controller is operatively connected to the plurality of flow control valves for controlling the flow of the extracted landfill gas out of the plurality of gas extraction well heads.

In one embodiment, the system for monitoring or controlling an aerobic landfill bioreactor further comprises a human machine interface operatively connected to the controller for displaying at least one of: the measured temperature, the measured relative humidity, and the detected at least one gas constituent.

In one embodiment, the aerobic landfill bioreactor further comprises at least one injection well head, and the system for monitoring or controlling an aerobic landfill bioreactor further comprises: a liquid injection system configured for injecting liquid into the aerobic landfill bioreactor via the at least one injection well head; and an air injection blower configured for injecting air into the aerobic landfill bioreactor via the at least one injection well head.

In one embodiment, the liquid injection system is operatively connected to the controller; and the controller actuates the liquid injection system based on at least one of: the measured temperature, the measured relative humidity, and the at least one detected gas constituent.

In one embodiment, the air injection blower is operatively connected to the controller; and the controller controls the flow rate of the air injection blower based on at least one of: the measured temperature, the measured relative humidity, and the at least one detected gas constituent.

In one embodiment, the aerobic landfill bioreactor comprises a plurality of zones, the at least one injection well head comprises a plurality of gas extraction well heads with at least one injection well head in each of the plurality of zones, the air injection system further comprises an air injection zone header including a plurality of isolation valves configured for isolating at least one of the plurality of zones, and the liquid system further comprises a liquid injection zone header including a plurality of isolation valves configured for isolating at least one of the plurality of zones.

In another aspect of the present invention, there is provided a method of monitoring or controlling an aerobic landfill bioreactor, comprising: extracting a landfill gas from the landfill bioreactor via at least one gas extraction well head, measuring a temperature of the extracted landfill gas in the at least one gas extraction well head, measuring a relative humidity of the extracted landfill gas, measuring a concentration of at least one gas constituent of the extracted landfill gas, and determining at least one operating condition of the aerobic landfill bioreactor based on the measured temperature, relative humidity, and at least one of the plurality of gas constituents.

In one embodiment, the method further comprises: measuring initial leachate condition to determine the initial amount of moisture in the aerobic landfill bioreactor, measuring liquid infiltrating into the aerobic landfill bioreactor, and conducting a water balance computation to determine an upper humidity limit and a lower humidity limit. The lower relative humidity limit indicates that insufficient moisture is being drawn from the bioreactor thus increasing moisture content. The upper relative humidity limit indicates that too much moisture is being drawn from the bioreactor thus decreasing its moisture content.

In one embodiment, the method further comprises controlling at least one of: liquid and air being injected into the aerobic landfill bioreactor based on the at least one operating condition.

In one embodiment, the aerobic landfill bioreactor is comprised of a plurality of zones, and the method further comprises configuring a header system to isolate zones such that the controlling at least one of liquid and water is done for only zones having the operating condition.

In one embodiment, the at least one constituent comprises oxygen.

In another embodiment, the at least one gas constituent comprises carbon monoxide.

In yet another embodiment, the at least one gas constituent comprises oxygen and carbon monoxide.

In one embodiment, the method further comprises: if the measured temperature is greater than a lower temperature limit and less than an upper temperature limit, and if the oxygen in the extracted landfill gas is less than a lower oxygen percentage limit then increasing a flow of air through the aerobic landfill bioreactor.

In one embodiment, the method further comprises: if the measured temperature is greater than a lower temperature limit and less than an upper temperature limit, if the oxygen in the extracted landfill gas is greater than a lower oxygen percentage limit and less than an upper oxygen percentage limit, and if the carbon monoxide is present in the extracted landfill then increasing a flow of air into the aerobic landfill bioreactor.

In one embodiment, the method further comprises: if the measured temperature is less than a lower temperature limit, and if the oxygen in the extracted landfill gas is less than a lower oxygen percentage limit then increasing a flow of air into the aerobic landfill bioreactor.

In one embodiment, the method further comprises: if the measured temperature is less than a lower temperature limit, if the oxygen in the extracted landfill gas is greater than a lower oxygen percentage limit and less than an upper oxygen percentage limit, and if the carbon monoxide is present in the extracted landfill gas then increasing a flow of air into the aerobic landfill bioreactor.

In one embodiment, the method further comprises: if the measured temperature is less than a lower temperature limit, if the oxygen percentage in the extracted landfill gas is greater than a lower oxygen percentage limit and less than a higher oxygen percentage limit, if the carbon monoxide is not present in the extracted landfill gas, and if the measured relative humidity is greater than the upper relative humidity limit then adding liquid to the aerobic landfill bioreactor.

In one embodiment, the method further comprises: if the measured temperature is less than a lower temperature limit, if the oxygen percentage in the extracted landfill gas is greater than an upper oxygen percentage limit, and if carbon monoxide is not present in the extracted landfill gas then performing a test for completeness.

In one embodiment, the method further comprises: if the measured temperature is less than a lower temperature limit, if the oxygen percentage in the landfill gas is greater than an upper oxygen percentage limit, and if the carbon monoxide is present in the extracted landfill gas, and if the measured relative humidity is less than the lower relative humidity limit then adding liquid to the aerobic landfill bioreactor.

In one embodiment, the method further comprises: if the measured temperature is less than a lower temperature limit, if the oxygen in the extracted landfill gas is greater than an upper oxygen percentage limit, if the carbon monoxide is present in the extracted landfill gas, and if the measured relative humidity is greater than the upper relative humidity limit then decreasing the flow of air into the aerobic landfill bioreactor.

In one embodiment, the method further comprises: if the measured temperature is greater than a lower temperature limit and less than an upper temperature limit, if the oxygen in the extracted landfill gas is greater than an upper oxygen percentage limit, if the carbon monoxide is present in the extracted landfill gas, and if the measured relative humidity is less than the lower relative humidity limit then adding liquid to the aerobic landfill bioreactor.

In one embodiment, the method further comprises: if the measured temperature is greater than a lower temperature limit and less than an upper temperature limit, if the oxygen in the extracted landfill gas is greater than an upper oxygen percentage limit, and if the carbon monoxide is not present in the extracted landfill gas, then performing a test for completeness.

In one embodiment, the method further comprises: if the measured temperature is greater than a lower temperature limit and less than an upper temperature limit, if the oxygen in the extracted landfill gas is greater than an upper oxygen percentage limit, if the carbon monoxide is present in the extracted landfill gas, and if the measured relative humidity is greater than the upper relative humidity limit then increasing the flow of air into the aerobic landfill bioreactor.

In one embodiment, the method further comprises: if the measured temperature is greater than an upper temperature limit, and if the carbon monoxide is present in the extracted landfill gas then adding liquid to the aerobic landfill bioreactor.

In one embodiment, the method further comprises: if the measured temperature is greater than an upper temperature limit, and if the carbon monoxide is not present in the extracted landfill gas, then the system is stopped and the air flow into the aerobic landfill bioreactor is slowly restarted.

DETAILED DESCRIPTION OF THE EMBODIMENTS

In view of the problems discussed in the background, it is therefore an object of this disclosure to provide for systems and methods to monitor the operation of an aerobic landfill bioreactor by accurately measuring the main operating conditions identified earlier, namely: temperature, moisture content, and gas constituent concentrations. It is another object of the present invention to provide for systems and methods to optimize the injection of air and liquid into an aerobic landfill bioreactor while maintaining the aforementioned operating conditions in optimal ranges. It is yet another object of the present invention to provide for systems and methods to facilitate the degradation of the labile organic fraction of the municipal solid waste in a landfill while avoiding methane production and minimizing or eliminating leachate production.

In this disclosure, the following terms may be used interchangeably: aerobic bioreactor, aerobic landfill bioreactor, aerobic landfill bioreactor cell, and aerobic landfill bioreactor site.

System for Monitoring and Controlling an Overdrawing Aerobic Landfill Bioreactor's Operation With reference to FIG. 1A, a system 100 for monitoring the operating conditions of an aerobic landfill bioreactor is provided. In the simplified system shown, an aerobic landfill bioreactor cell is comprised of two zones 102 and 122. Each zone has two gas extraction well heads 110. Each of gas extraction well heads 110 is connected to a gas extraction zone header 115 and 125 via a flow control valve 104 and 124. Flow control valves 104 and 124 controls the extraction rate of landfill gases from the well head 110 to which it is connected. Additionally, all gas extraction well heads 110 in a particular zone are connected (in fluid communication) via the gas extraction pipes, to a header specific to that particular zone. For example, all gas extraction well heads 110 in zone 102 are connected to gas extraction header 115. Similarly, all gas extraction well heads 110 in zone 122 are connected to gas extraction zone header 125. Gas extraction zone headers 115 and 125 can allow gas extraction from select zones, while disallowing it from other zones. This is done by means of opening or closing isolation valves associated with each header, such as isolation valve 116 to gas extraction zone header 115, and isolation valve 126 to gas extraction zone header 125.

Gas extraction zone headers 115 and 125 are fluidly connected to a main header 130, which connects it to gas extraction system for extracting landfill gas from the aerobic landfill bioreactor. The gas extraction system is comprised of a number of components: relative humidity detector 150, gas constituent detector 160, and gas extraction blower 190. The gas extraction blower 190 is configured to draw landfill gas out of the aerobic landfill bioreactor via the gas extraction well heads 110. For example, the gas extraction blower 190 generates suction in the main header 130, through any open headers (115, 125, or both), and into the gas extraction well heads 110. The generated suction helps draw landfill gases out of the landfill cell zone via gas extraction well heads 110 which are connected to the open header(s). The relative humidity detector 150 is configured to measure the relative humidity of the extracted landfill gas. The gas constituent detector 160 is configured to detect at least one gas constituent of the extracted landfill gas. A controller 170 is configured for: receiving the measure temperature from temperature sensors 108, receiving the measured relative humidity from relative humidity detector 150, receiving the detected, at least one, gas constituent from gas constituent detector 160, and controlling the gas extraction blower 190.

Figure 1B:
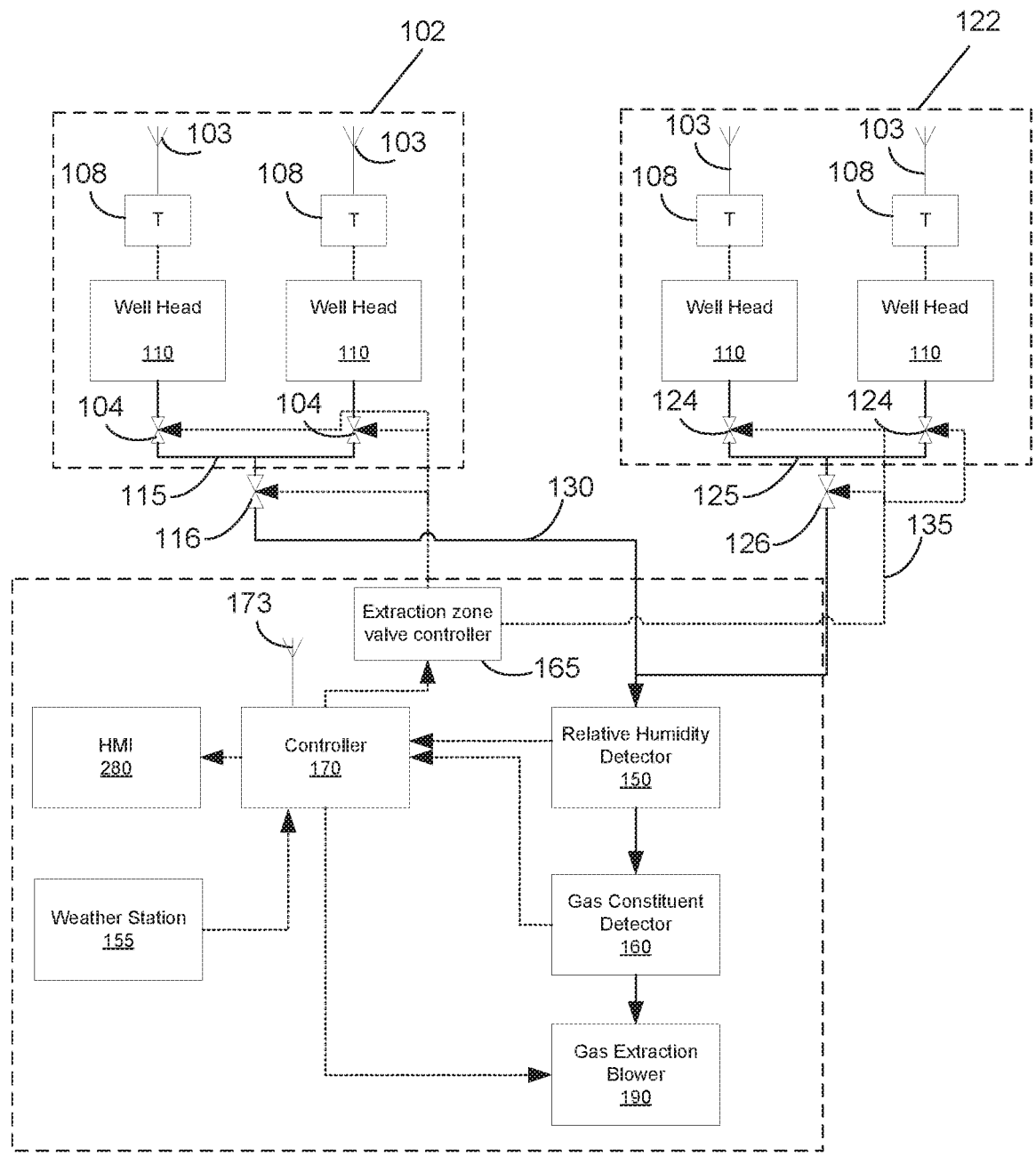
FIG. 1B is a block diagram of a system similar to that of FIG. 1A but also featuring gas extraction zone valve control, in accordance with another embodiment of the present invention.

To monitor the temperature in the aerobic landfill bioreactor, temperature sensors 108 are provided or disposed in the gas extraction well heads 110 for measuring the temperature of the extracted landfill gas. In one embodiment, temperature sensors 108 have telemetric capability so they can report their readings to a remote system component, such as controller 170, as shown in FIGS. 1A-1B, and FIG. 2. For example, temperature sensors 108 may have cellular connectivity and may each be provided with an antenna 103 and a cellular radio (not shown). Alternatively, the temperature sensors may have a Wi-Fi radio (not shown), and the landfill site may have a Wi-Fi access point (not shown) or hot spot for providing connectivity to a wide area network such as the internet. In yet another embodiment (not shown), the temperature sensors 108 may be connected to telephone line via a modem or otherwise for sending temperature measurements over a wired telephone system.

The measured temperature values from the various gas extraction well heads in various zones are communicated, either wirelessly or in a wired manner, to a central controller. In the depicted embodiment the controller 170 also features an antenna 173 so that it may communicate with temperature sensors 108 wirelessly either over a cellular connection or a Wi-Fi connection, or any other suitable means such as satellite communications. Controller 170 may be a computing device such as a programmable logic controller (PLC), a desktop computer, laptop computer, server, table, mobile phone, smart phone, or the like. Controller 170 may contain computer instructions, which enable it to analyze the measured temperature and report whether it is in a particular desired range. Controller 170 may contain a built-in display or may be operatively connected to an external human machine interface (HMI) 280 which may comprise a display, keyboard, mouse or other input devices operative connected thereto. HMI 280 is operatively connected to the controller 170 for displaying at least one of: measured temperature, relative humidity, and gas constituent value. Controller 170 may also be operatively connected to gas extraction blower 190 in order to control the rate at which gas extraction blower 190 operates.

Figure 3A:
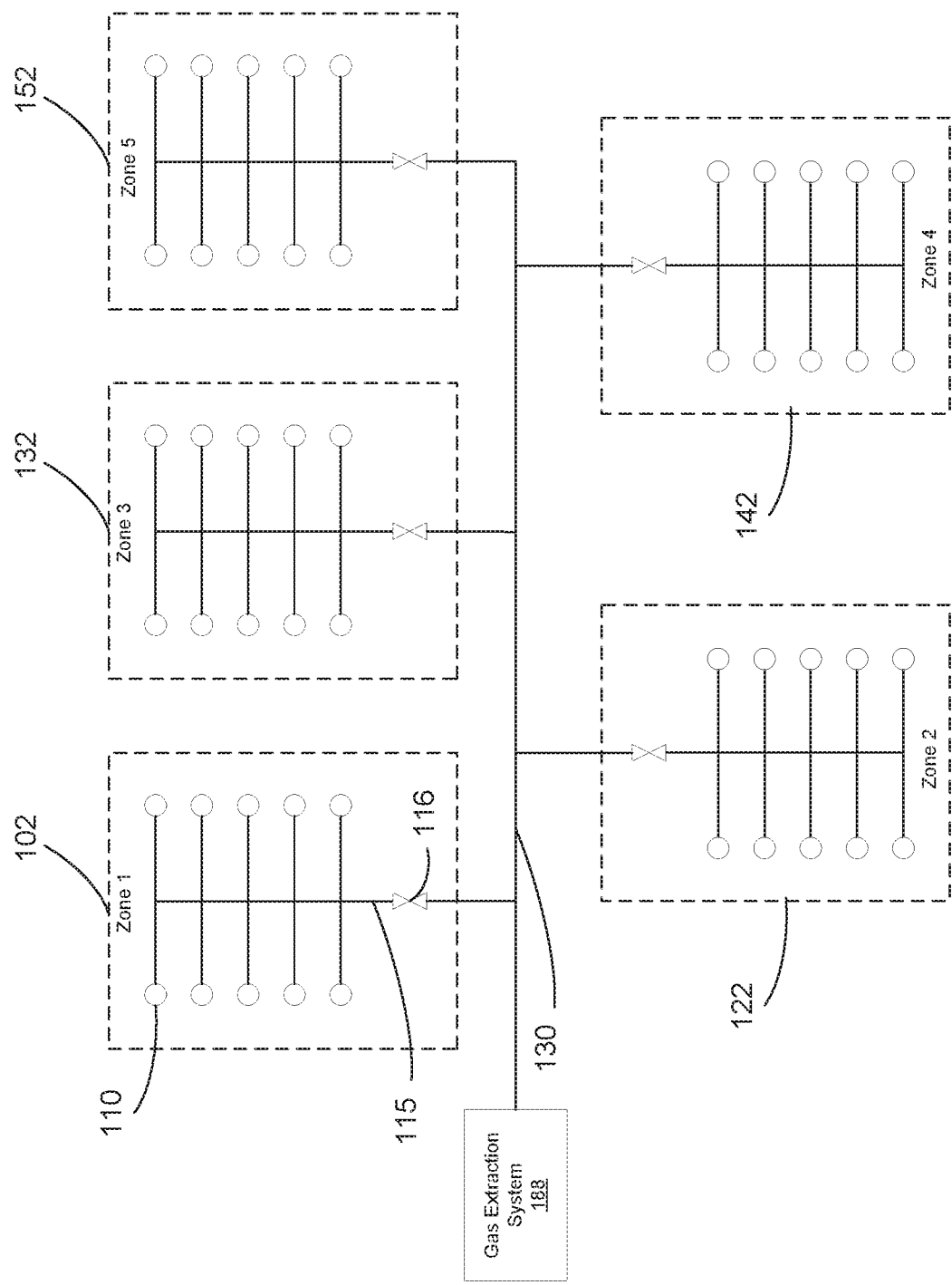
FIG. 3A is a system diagram depicting an aerobic landfill bioreactor site comprised of a plurality of zones, each zone having a plurality of gas extraction well heads, and each zone being connected to a gas extraction system via a gas extraction header, in accordance with an embodiment of the present invention.

The number of zones and well heads shown in FIGS. 1A and 1B are for ease of illustration only. A person skilled in the art would understand that system 100 is applicable to an aerobic landfill bioreactor cell that is comprised of any number of zones. Similarly, each aerobic landfill bioreactor cell zone may have more well heads. FIG. 3A is a system diagram depicting an aerobic landfill bioreactor site comprised of five zones: 101, 122, 132, 142, and 152. Each zone has a plurality of gas extraction well heads 110. Each zone is connected to the gas extraction system 188 via a gas extraction header 130 and an isolation valve 116. The gas extraction system 188 is comprised of a gas extraction blower, a relative humidity detector, and a gas constituent detector.

Figure 4A:
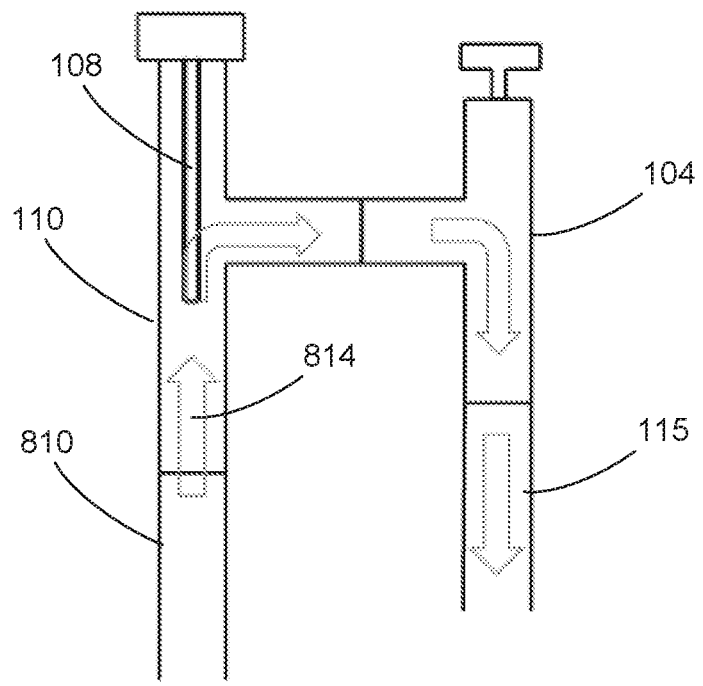
FIG. 4A is a side sectional view of a gas extraction well head.

FIG. 4A shows a side sectional view of a gas extraction well head 110 along with a flow control valve 104 and temperature sensor 108. The temperature sensor 108 is positioned near the top of the well head 110. However, a person skilled in the art would appreciate that the temperature sensor may be located anywhere in the well head without materially affecting the accuracy of the measurement. The flow of the landfill gas being extracted is depicted by arrows 814. The landfill gas flows out of the well 810 into well head 110 where it comes into contact with temperature sensor 108. The gas then flows through the flow control valve 104 and into gas extraction zone header 115.

Turning back to FIG. 1A, the system 100 involves real-time temperature monitoring by temperature sensors 108 at every active gas extraction well head 110. This achieves an amalgam measurement of the temperature in the landfill. The extracted landfill gas will have come from regions having active biological activity and therefore gives a most precise representation of the landfill cell temperatures as a whole. Since the landfill gas temperature is measured directly at the surface of the landfill, it is expected that the temperature will not yet be affected by ambient air. Advantageously, the ex-situ placement of the temperature sensors 108 in the gas extraction well heads 110 gives temperature measurements which are more accurate than temperature measurements from in-situ sensors placed within the landfill which are only representatives of temperatures in the vicinity of the sensors.

The various temperature sensors are each provided with a unique identifier thus enabling the controller 170 to uniquely identify the well head, and accordingly the zone, from which a particular temperature reading originated.

The moisture and gas constituent concentrations of the extracted landfill gas are measured at a central location. Isolation valves 116 and 126 can be used to isolate selected zones from the landfill cell to ensure that measured parameters are from other zones. For example, assuming that initially both gas extraction zone headers 115 and 125 are active. In other words, respective isolation valves 116 and 126 are open. The relative humidity of the extracted landfill gas is measured by relative humidity detector 150. If the relative humidity detector 150 reports relative humidity outside of the desired range in the extracted landfill gas, isolation valve 126 can be closed to isolate zone 122, ensuring that the extracted landfill gas comes from zone 102 only. Then if the measured relative humidity returns to the desired range, it is inferred that zone 102 is not experiencing the moisture issues, and that the zone causing the moisture concerns is likely zone 122. Isolation valve 116 can then be used to isolate zone 102 and isolation valve 126 can be opened to connect zone 122 to the main header 130. If the measured relative humidity moves out of the desired range again, then it is ascertained that zone 122 is contributing to the moisture concerns. Similarly, if a gas constituent concentration outside of the normal range is detected, the header system may also be used in the same manner to identify the zone producing that gas constituent concentration. Advantageously, in a landfill cell having a number of zones, the system of headers can isolate one zone at a time in order to identify the zone(s) experiencing a particular operating condition.

The system 100 permits monitoring of moisture (by measuring relative humidity) in the extracted landfill gas, as well as monitoring the gas constituent concentrations of the extracted landfill gas. In the shown embodiment, the extracted gas is first passed through relative humidity detector 150 where the relative humidity is measured. The gas is then passed through gas constituent detector 160. Each of the relative humidity detector 150 and gas constituent detector 160 are in communication with controller 170, through suitable means, in order to communicate the measured relative humidity and gas constituent concentrations thereto. For example, both detectors may have a wired serial or parallel interface, a network interface such as Ethernet, or a wireless interfaces such as Wi-Fi or Bluetooth.

The relative humidity of the landfill gas is measured by relative humidity detector 150 to determine the volume of liquid that is being removed from the landfill by evaporation into the extracted landfill gas. Monitoring the amount of liquid lost from the landfill cell can be used to characterize the state of the landfill, and to determine the amount of liquid that needs to be added to maintain adequate moisture content within the system. The heterogeneity of landfills can create localized zones of moisture content within the system; therefore the installation of in-situ moisture sensors in the landfill mass may not give an accurate measure of the overall moisture within the landfill cell. Advantageously, measuring the relative humidity of the extracted landfill gas is not affected by this heterogeneity of the landfill cell, and accordingly provides a more accurate estimation of the overall moisture therein.

While the relative humidity detector 150 and the gas constituent detector 160 are shown as separate components in FIG. 1A, they may be implemented as a single system component in some embodiments. Other embodiments of the invention could include the relative humidity detector 150 and the gas constituent detector 160, or a single system combining these two components disposed at the well heads for direct measurement at each well location.

FIG. 1B shows a system 100 similar to that of FIG. 1A but additionally features automatic header isolation valve 116 and 126, as well as automatic flow control valve 104 and 124, controls. In addition to the system components already described with reference to FIG. 1A, an extraction zone valve controller 165 is operatively connected to the gas extraction zone isolation valves 116 and 126, as well as flow control valves 104 and 124, so that one or more isolation valves (116 or 126), or flow control valves (104 or 124), may be activated or deactivated to isolate or connect a respective zone (102 or 122) or modify flow rates at wells within zones. This is done via control line 135, which is shown as a dotted line between extraction zone valve controller 165 and both isolation valves 115 and 125 and all flow control valves 104 and 124. Advantageously, in a landfill cell having a number of zones, the system of gas extraction zone headers and a valve controller can isolate one zone at a time in order to identify the ones experiencing a particular operating condition in an automated manner. The extraction zone valve controller 165 may be controlled by receiving control signals from controller 170, as shown. Alternatively (not shown), the extraction zone valve controller 165 may be independently controlled. The extraction zone valve controller 165 may be a standalone component or may be an integral component of the controller 170.

Figure 2A:
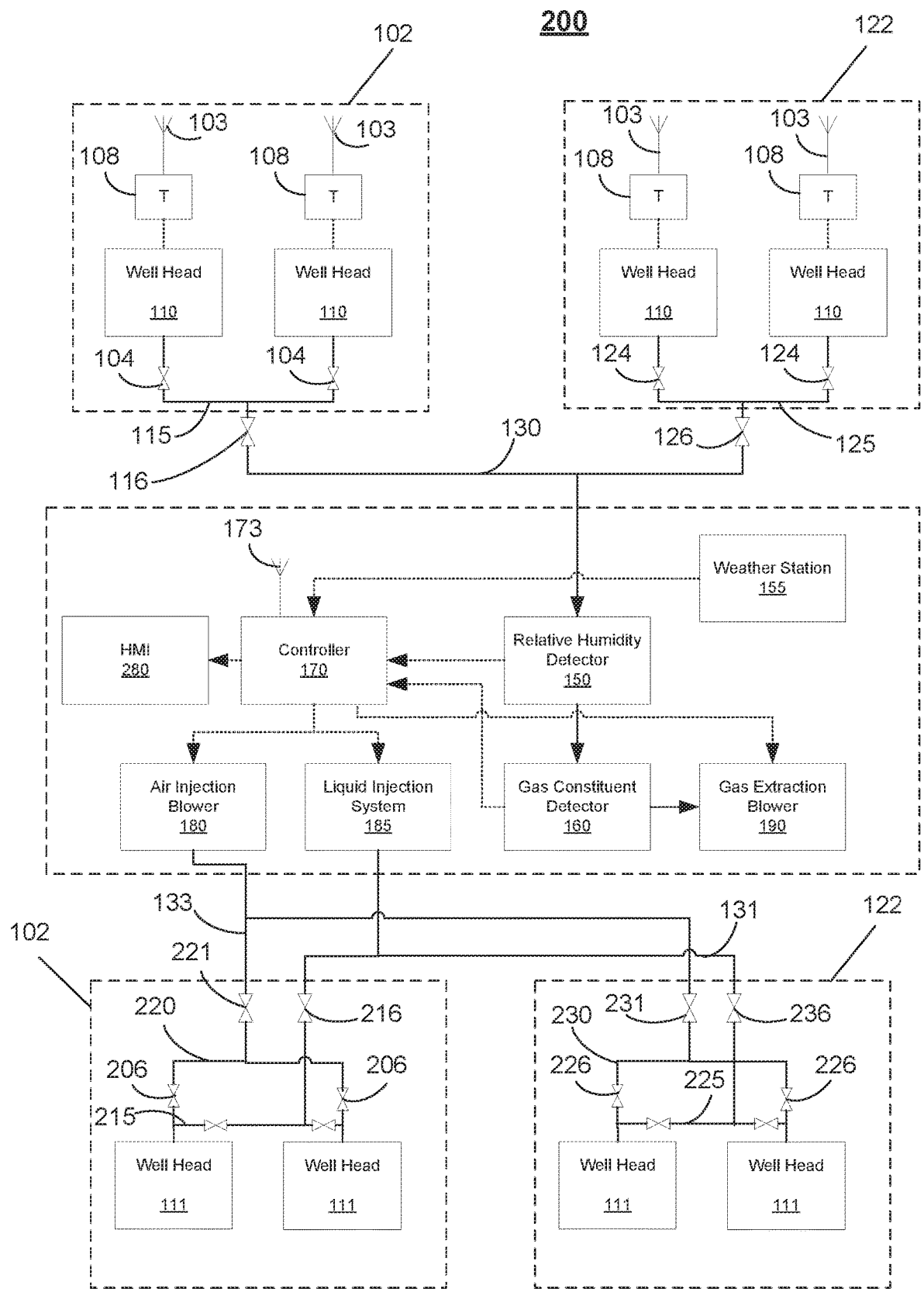
FIG. 2A is a block diagram of a system for monitoring and controlling the operation of an aerobic landfill bioreactor, in accordance with yet another embodiment of the present invention.

System for Monitoring and Controlling a Low Pressure Air Injection Aerobic Landfill Bioreactor Operation FIG. 2A depicts a system 200 for controlling and optimizing the operation of an aerobic landfill bioreactor. The system involves a minimal landfill cell of just two zones, for ease of illustration. It would be apparent to persons skilled in the art that the described system can be scaled to larger landfills comprised of multiple zones, and in which each of the zones includes a number of well heads. The system 200 comprises two zones 102 and 122. Each of the two zones has four well heads; two gas extraction well heads 110, and two air/liquid injection well heads 111. For ease of illustration, the gas extraction well heads 110 are separated from the injection well heads 111 in FIG. 2, however it would be understood by persons skilled in the art, that the two types of well heads may be placed in proximity to one another.

Gas extraction well heads 110, temperature sensors 108, flow control valves 104 and 124, and gas extraction zone headers 115 and 125 have all been described with respect to system 100 and therefore they will not be described in detail here. Injection well heads 111 have a similar structure to that of gas extraction well heads 110 with the exception that they do not have temperature sensors located therein.

The system 200 detects the operating conditions of the aerobic landfill bioreactor cell zones 102 and 122, by measuring temperature, moisture content, and gas constituent concentrations as described above with respect to system 100. Additionally, system 200 attempts to alter the conditions within the aerobic landfill bioreactor cell by injecting controlled amounts of air and/or liquid. As the operating conditions are reported to the controller 170, a few decisions may be made to vary the operating conditions.

The system 200 features an air injection blower 180, and a liquid injection system 185. The air injection blower 180 is configured for injecting air into the aerobic landfill bioreactor via the injection well heads 111. For example, the air injection blower 180 draws ambient atmospheric air, and pumps it to the air injection header 133. The liquid injection system 185 is configured for injecting liquid into the aerobic landfill bioreactor via the injection well heads 111. Liquid injection system 185 may be a pumping system which pumps water or another suitable liquid into the liquid injection header 131. In the depicted embodiment, air and liquid are using different header systems. For instance, liquid injection header 131 which conveys liquid from the liquid injection system 185 to injection well heads in the various zones of the bioreactor is connected to liquid injection zone header 215 (in zone 102), and liquid injection zone header 225 (in zone 122). Isolation valves 216 and 236 of liquid injection zone headers 215 and 225, respectively, can be used to isolate a respective zone so that no liquid is injected into that zone by the liquid injection system 185. Similarly, air injection header 133 which conveys air from the air injection blower 180 to the injection well heads 111 in the various zones of the bioreactor is connected to air injection zone header systems 220 (in zone 102) and 230 (in zone 122). Isolation valves 221 and 231 may be used to isolate a respective zone so that no air is injected into that zone by the air injection blower 180. Additionally, flow control valves 206 and 226 are provided in the injection well heads 111 of zones 102 and 122, respectively, and serve to control the flow of air injected to the individual well heads 111. The air injection blower 180 and liquid injection system 185 may each be independently or manually controlled. Alternatively, as shown in the depicted embodiment, air injection blower 180 and liquid injection system 185 may each or both be operatively connected to controller 170. If the liquid injection system 185 is operatively connected to the controller 170, then controller 170 may actuate the liquid injection system 185 based on at least one of: the measured temperature, the measured relative humidity, and at least one detected gas constituent of the extracted landfill gas. If the air injection blower 180 is operatively connected to the controller 170, then controller 170 may control the flow rate of the air injection blower based on at least one of: the measured temperature, the measured relative humidity, and at least one detected gas constituent of the extracted landfill gas.

As an example, the controller 170 may determine, from relative humidity detector 150, as described above, that a particular zone has low moisture. For example, zone 122 may have low moisture as determined by the relative humidity detector 150 when only gas extraction header 125 was open. To rectify the problem, liquid needs to be added to zone 122. Accordingly, isolation valve 236 is open while isolation valve 216 is closed. This ensures that the additional liquid is added to zone 122 but not zone 102. Next the liquid injection system 185 is activated to pump liquid via liquid injection header 131, through liquid injection zone header 225 to the well heads 111 of zone 122. In one embodiment, the liquid injection system 185 is manually activated to pump the additional liquid. In another embodiment, the controller 170 activates liquid injection system 185 so that it pumps the additional liquid. The relative humidity is measured again and if it indicates that the moisture content of zone 122 has become adequate, then the liquid injection system 185 may be deactivated.

Similarly, if it is determined from measurements taken by the gas constituent detector 160 that oxygen is low in zone 102, then air flow is increased in that zone. The flow rate of the air injection blower 180 is increased. Flow control valves 206 are modified to increase the flow of injected air into well heads 111 of zone 102. When the rate of injecting air into a zone is increased, this is generally accompanied by a corresponding increase in the gas extraction rate of the same zone. Accordingly, the controller 170 typically controls air injection blower 180 and gas extraction blower 190 together to ensure smooth flow of gas through the various bioreactor zones, and flow control valves 104 are modified to increase gas collection rates from zone 102.

Figure 3B:
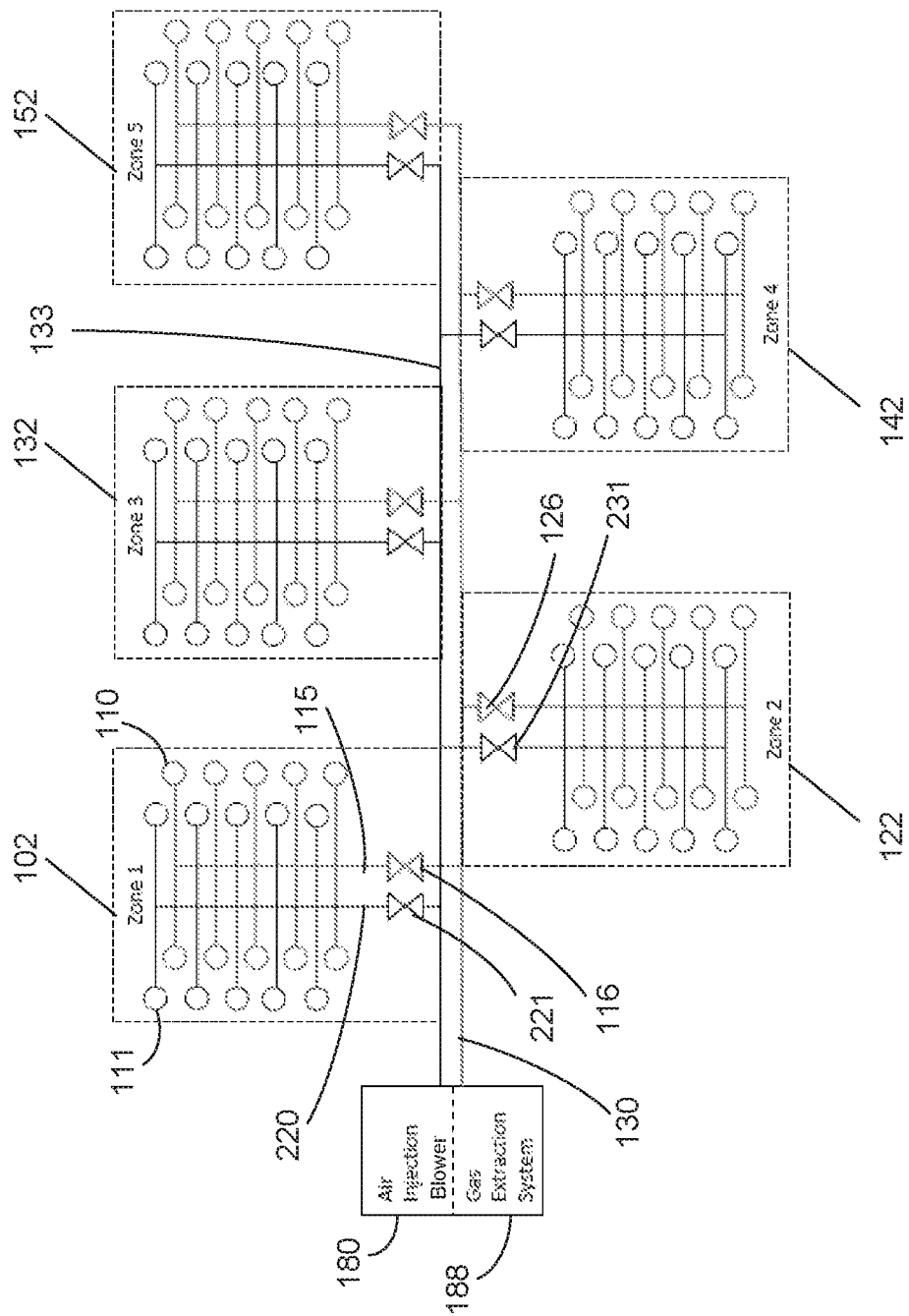
FIG. 3B is a system diagram depicting an aerobic landfill bioreactor site comprised of a plurality of zones, each zone having a plurality of injection well heads and gas extraction well heads, and each zone being connected to an air injection system and to a gas extraction system via a respective header, in accordance with another embodiment of the present invention.

FIG. 3B is a system diagram depicting an exemplary aerobic landfill bioreactor site comprised of 5 zones 102, 122, 132, 142, and 152. Each of the 5 zones has ten injection well heads 111, and 10 gas extraction well heads 110. The injection well heads 111 of each of the 5 zones are connected to the main air injection header 133 via air injection zone headers. For example header 220 connects zone 1 (102) through the air injection isolation valve 221 to the air injection header 133. Main air injection header 133 connects to air injection blower 180. Any of the 5 zones may be isolated from the air injection blower 180 by closing a respective air injection isolation valve. Similarly, the gas extraction well heads 110 of each of the 5 zones are connected to the main gas extraction header 130 via gas extraction zone headers. For example header 115 connects zone 1 (102) through the gas extraction isolation valve 116 to the main gas extraction header 130 and finally to the gas extraction system 188. Any of the 5 zones may be isolated from the gas extraction system 188 by closing a respective isolation valve. The diagram does not include a liquid injection system for simplicity. A liquid injection system may use the same headers as the air injection system, but with activating only one of them at a given time. Alternatively, a separate header system may be used for each of the air and liquid injection systems.

Figure 4B:
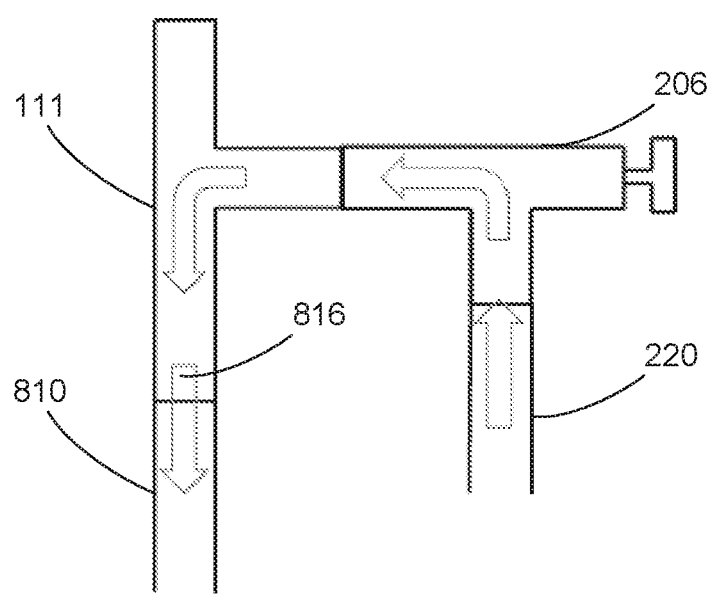
FIG. 4B is a side sectional view of an injection well.

FIG. 4B is a side sectional view of an injection well head 111. The flow of air/liquid through the injection well head 111 is denoted by arrows 816. The flow control valve 206 controls the rate of injection of the liquid or air into the well head 111. Flow control valves 206 may each be manually controlled or remotely actuated by telemetry. The air or liquid flows from zone header 220 through the flow control valve 206, into the well head 111 and then into the well 810. In some embodiments, the flow control valve is rated for air only, and the liquid is injected into the well head at a point downstream of flow control valve 206, as shown in FIG. 2A, for example.

Figure 2B:
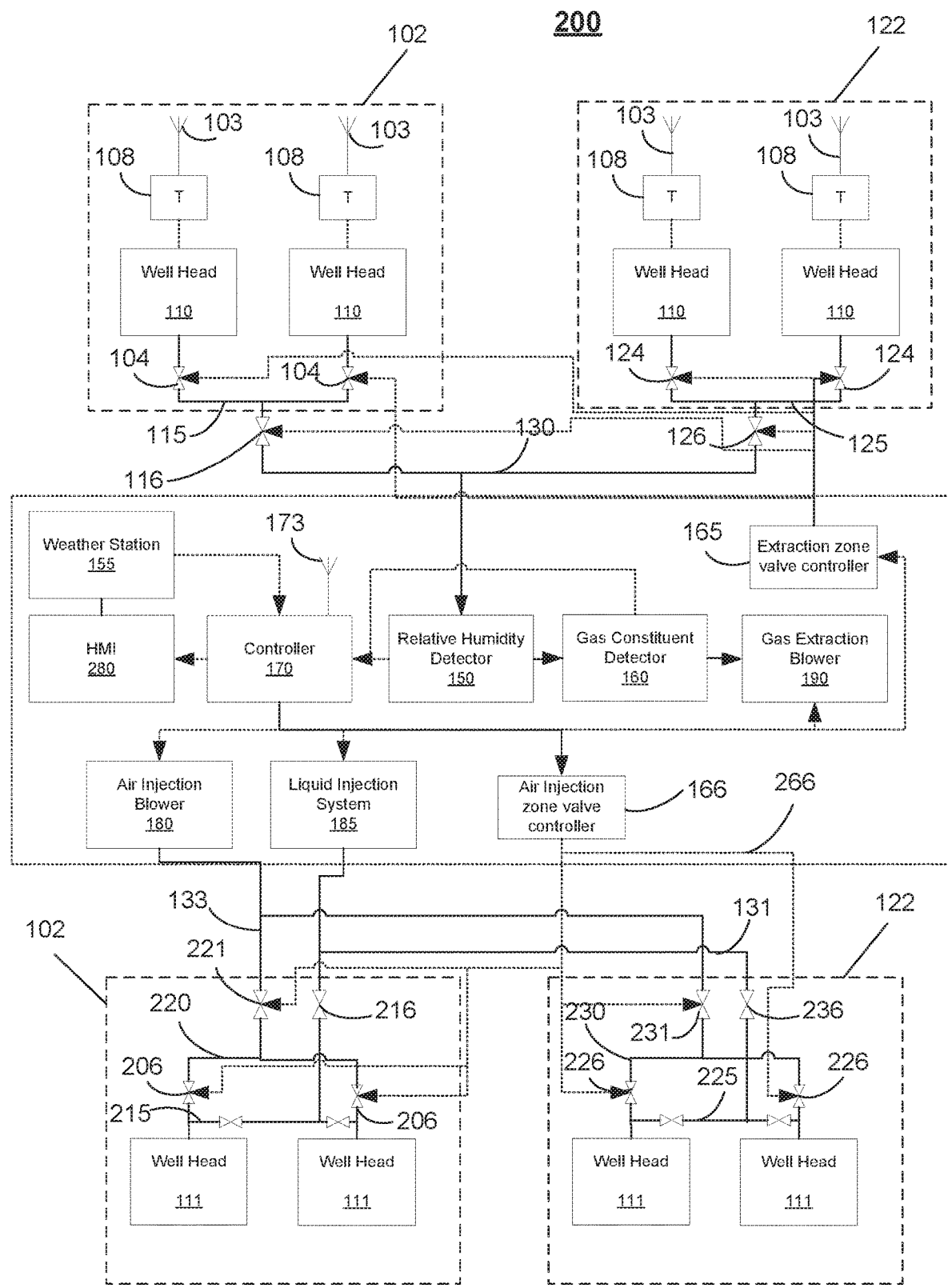
FIG. 2B is a block diagram of a system similar to that of FIG. 2A but also featuring zonal valve control, in accordance with yet another embodiment of the present invention.

FIG. 2B shows a system 200 similar to that of FIG. 2A but additionally features automatic header isolation valves 221 and 231 for the air injection system, and automatic header isolation valves 216 and 236 for the liquid injection system. The system also features automatic flow control valves 206 and 226. In addition to the system components already described with reference to FIG. 2A, an air injection zone valve controller 166 is operatively connected to the air injection zone isolation valves 221 and 231, as well as flow control valves 206 and 226, so that one or more isolation valves (221 or 231), or flow control valves 206 and 226, may be activated or deactivated to isolate or connect a respective zone (102 or 122) or modify flow rates at wells within zones. This is done via control line 266, which is shown as a dotted line between injection zone valve controller 166 and isolation valves 221, 231, 216 and 236 and all flow control valves 206 and 226. Advantageously, in a landfill cell having a number of zones, the system of injection zone headers and a valve controller can isolate one zone at a time in order to address particular operating condition in an automated manner. The injection zone valve controller 166 may be controlled by receiving control signals from controller 170, as shown. Alternatively (not shown), the injection zone valve controller 166 may be independently controlled. The injection zone valve controller 166 may be a standalone component or may be an integral component of the controller 170.

Controlling Temperature

The temperature in the landfill is controlled by the biological activity, as well as the dissipation of heat through either the injection of liquid (thermal mass), or the rate of pore space air replacement. The biologically mediated chemical reactions are exothermic in nature and therefore the more active the aerobic heterotrophic microorganisms are in the landfill, the higher the achievable temperature in the system is. Higher temperatures can also lead to greater activity rates in the microorganisms, further increasing reaction rates and therefore increasing temperatures. It is generally accepted that optimal aerobic activity in the landfill is achieved in the thermophilic range (45° C.-70° C.). Outside of this range the microbial consortia will shift species resulting in less efficient degradation of the organic material.

The air injection blower 180 can be used to modify the temperature in the landfill in multiple ways. For example, providing more air (and hence more oxygen) to the microorganisms to increase the biological activity in the landfill can increase temperatures. Conversely, decreasing the oxygen supply can decrease the biological activity. There is, however, a risk of some areas returning to anaerobic conditions if the oxygen supply is decreased too much. Increasing the air injection rate, and therefore the air flow through rate, can also serve to decrease the temperature by rapidly replacing the air in the void space, drawing off warm air and replacing it with colder ambient air.

Liquid injection can be used to decrease the temperature within the landfill through the injection of a greater thermal mass to help buffer the temperature changes. However, oversupply of liquid can result in void spaces becoming saturated with moisture. This can cause two separate concerns. First, saturated masses of solid waste can lead to leachate escape from the landfill due to the increased hydrostatic pressure on the liner system. Second, saturated zones can also block oxygen availability and create anaerobic zones, decreasing system efficiency while potentially returning these areas to methanogenic conditions.

Moisture/Relative Humidity

The moisture in the landfill is the bridge between the labile organic material and the aerobic heterotrophic microorganisms. The labile organic material must first go through a process of hydrolysis to have its components enter the aqueous phase, where they become the substrate for the growth of the microorganisms, followed by transport within the liquid to the microorganisms. If the landfill pore space were completely saturated with moisture, this transfer of substrate to the microorganisms would be optimized. However, as previously discussed the transfer of oxygen would then be minimized. Accordingly, there would be a risk of pooled leachate escaping the landfill, and anaerobic conditions occurring within the waste. The moisture content needs to be maintained in a range that is between the wilting point and the field capacity of the stored waste. In this range, there is sufficient moisture to allow a bridge between the solid substrate, and the microorganisms. This also negates the risks of ponding that may block oxygen transfer. Additionally, the risk of leachate release is eliminated.

Moisture is added to the system through the liquid injection system 185, as discussed earlier, but moisture will also be produced in the landfill as the labile organic material is degraded and moisture is released. Moisture is removed from the system through the extraction of the produced gasses by landfill gas extraction blower 190. The warm gasses that are removed to allow for more air injection are typically saturated with moisture due to the high temperatures in the system. Controlling the air injection rate, and therefore the gas extraction rate, can help control the overall moisture loss from the stored waste.

The desired relative humidity of the extracted landfill gas is a site specific quantity that is determined through a water balance computation conducted at the site. The initial leachate condition is measured prior to system startup to determine the initial amount of moisture in the aerobic landfill bioreactor cell. During aerobic landfill bioreactor operation this initial moisture content is paired with the data from a local weather station 155 that is used to determine the precipitation and accordingly the infiltration of moisture into the aerobic landfill bioreactor cell. The weather station 155 may include one or more rain gauges for measuring precipitation. For example a tipping bucket rain gauge may be used, as part of the weather station, to measure the precipitation at the landfill site. Alternatively, other precipitation measuring means such as weather radar, or satellite imagery may be used to measure precipitation which accordingly gives an indication of the amount of infiltration of moisture into the aerobic landfill bioreactor cell. The moisture required for organic matter hydrolysis and the moisture produced through the final oxidation process are also accounted for, as well as the moisture injected via the liquid injection system 185. This water balance is used to determine what is considered a "low" or "high" relative humidity value based on the moisture requirements in the aerobic landfill bioreactor.

The relative humidity of the landfill gas is measured by relative humidity detector 150 to determine the volume of liquid that is removed from the landfill by evaporation into the extracted gas. This technique will not allow direct measurement of the moisture within the stored waste; however, monitoring the amount of liquid lost from the cell can be used to determine the amount of liquid that needs to be added to maintain adequate moisture content within the system. The heterogeneity of landfills can create localized zones of moisture and specific ponding locations; therefore even the installation of a sensor in the landfill mass may not give an accurate measure of the overall moisture within the system. The measurement and use of exhaust gas relative humidity is therefore a preferable option to more precisely identify moisture requirements within the aerobic landfill bioreactor.

Gas Constituents

The available oxygen in the landfill is the final component that needs to be controlled to optimize the aerobic landfill efficiency. The oxygen requirements are variable as the aerobic landfill bioreactor process progresses. Therefore, the air injection rate must also be varied. During the initial stages of aerobic landfill bioreactor operation, there are a small number of aerobic heterotrophic microorganisms present, and therefore the volumes of oxygen required are small. The number, and activity, of the aerobic heterotrophic microorganisms increase as the aerobic landfill matures. This increase in number and activity of the organisms increases the oxygen requirements. During the final stages of the aerobic landfill bioreactor, the quantity of organic substrate decreases, and so does the activity and number of aerobic heterotrophic microorganisms. Therefore the oxygen requirements also decrease.

Providing an overabundance of oxygen does not adversely affect the microorganisms due to the increased oxygen content. However, the higher flow through rates result in greater moisture loss, and a potential cooling of the landfill waste, which decrease treatment efficiency, and result in energy inefficiencies during system operation.

Current practices suggest the use of in-situ monitoring of oxygen content through the installation of multiple sensors throughout the landfill site. As discussed earlier, the sensors are only capable of obtaining readings in their vicinity, and the heterogeneity of the site renders many of those readings inaccurate and non-representative.

The present invention utilizes the extracted gasses, which are the by-products of the biologically mediated chemical reaction, from the landfill as an analogue to determine the biological activity levels in the landfill. Extracted gas constituent concentrations, detected by gas constituent detector 150, are used to determine the degree of completion of the biologically mediated chemical reactions, the oxygen availability, and the presence of anaerobic zones within the landfill. Gas constituent detector 150 is capable of detecting the presence of the following gases in the extracted landfill gas: methane, oxygen, carbon dioxide, and carbon monoxide.

Methane

Methane concentrations in the extracted landfill gas indicate the presence of anaerobic regions in the landfill. Once methane is detected in the extracted gas, the gas extraction isolation valves (e.g. 116 and 126) can be used to sequentially isolate the zones within the landfill and identify the anaerobic region, at which point the air injection rate can be increased in the anaerobic region by adjusting the air injection blower 180 and the flow control valves (e.g. 206, 226) at the injection well heads 111 and the gas extraction wells 110 (e.g. 104, 124) of the specific zone to stop anaerobic conditions. Should the anaerobic conditions persist, further monitoring of zone temperatures using sensors 108 and the relative humidity of the extracted landfill gas can be used to determine if there are concerns related to microbial growth that need to be addressed through the addition of moisture leading to anaerobic conditions.

Carbon Monoxide

Measuring carbon monoxide, carbon dioxide, and oxygen concentrations in the extracted gas demonstrates the completion extent of the biologically mediated chemical reactions. During the degradation of labile organic material, oxygen is consumed and organic carbon is converted to carbon dioxide. If there is insufficient oxygen in the aerobic landfill bioreactor, a fraction of the organic carbon in the waste is converted to carbon monoxide without being fully converted to carbon dioxide. Carbon monoxide presence in the extracted landfill gas is indicative of areas within the landfill that are not being supplied with sufficient oxygen for the complete conversion of the waste. In this case more oxygen is required to be supplied to ensure complete conversion is achieved. The determination of the zones with insufficient oxygen is achieved in the same fashion as the determination of anaerobic zones, the gas extraction isolation valves (e.g. 116 and 126) are used to isolate the zones of concern until the zone(s) of insufficient oxygen is determined. In response to identifying the zone, flow control valves (e.g. 104 and 206, or 124 and 226) are adjusted to increase airflow to the zone(s) of insufficient oxygen. The controller also actuates the air injection blower 180 and the gas extraction blower 190 to supply sufficient volumes of oxygen.

The monitoring of carbon monoxide and injection of air can be done continually until the presence of carbon monoxide is reduced to acceptable levels or carbon monoxide is absent from the extracted landfill gas.

Carbon Dioxide

Carbon dioxide is the highest concentration gaseous by-product from the aerobic degradation of the waste, and can therefore be used to help determine the maximum achievable biological activity in an aerobic landfill bioreactor. Carbon dioxide also indicates when the stored waste has been stabilized and no more biological activity can be achieved. The maximum biological activity is reached when a steady concentration of carbon dioxide is present in the extracted gas, while there is still available oxygen in the landfill gas.

Oxygen

Oxygen is monitored to ensure that there is excess oxygen in the landfill gas. A small concentration of excess oxygen in the landfill gas, approximately 5%, demonstrates that oxygen is not the limiting reagent in the system. If the excess oxygen in the landfill gas is higher than 5%, too much air is being supplied, at an additional wasted cost and stress on the equipment.

FIGS. 5A-5E collectively depicts steps of a method of controlling the operation of an aerobic bioreactor landfill, in accordance with another aspect of the present invention.

Figure 5A:
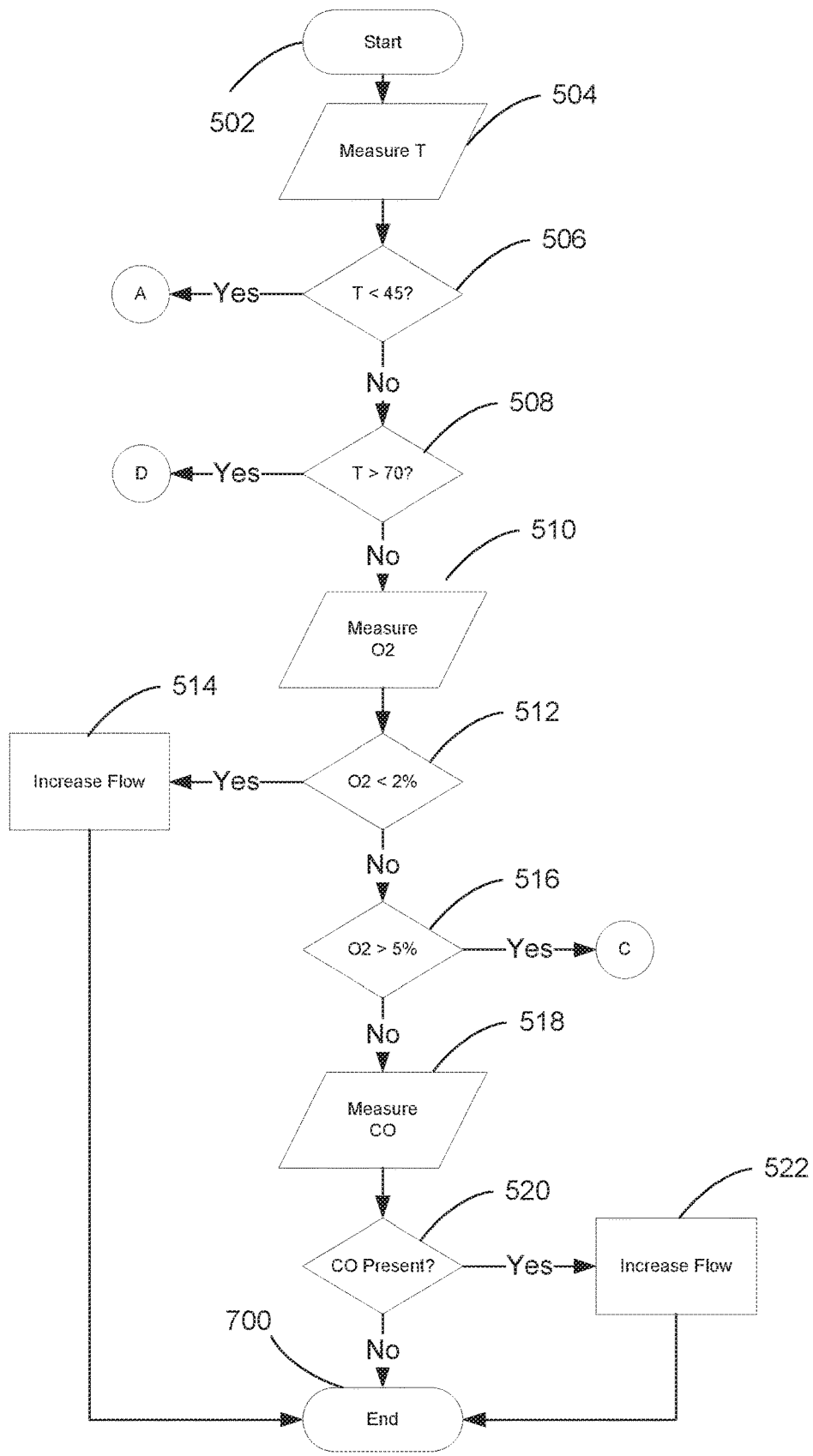
FIGS. 5A-5E depict a method of controlling an aerobic landfill bioreactor, in accordance with an embodiment of the present invention.

The method starts at step 502 in FIG. 5A. At step 504 the temperature (T) is measured using the plurality of temperature sensors 108 positioned in the gas extraction well heads 110 as discussed above. For each measured temperature, corresponding to a well head in a zone, a comparison is made to a lower limit temperature and an upper limit temperature to determine whether the corresponding region for the well head is operating in an optimal temperature range. Accordingly, at step 506 the measured temperature (T) is checked to see if it is lower than a predetermined lower temperature limit such as 45 degrees Celsius. If that is the case, control goes to step 530 on FIG. 5B where there is control logic, which is carried out to handle cases where the bioreactor temperature is below the predetermined lower temperature limit.

Figure 5B:
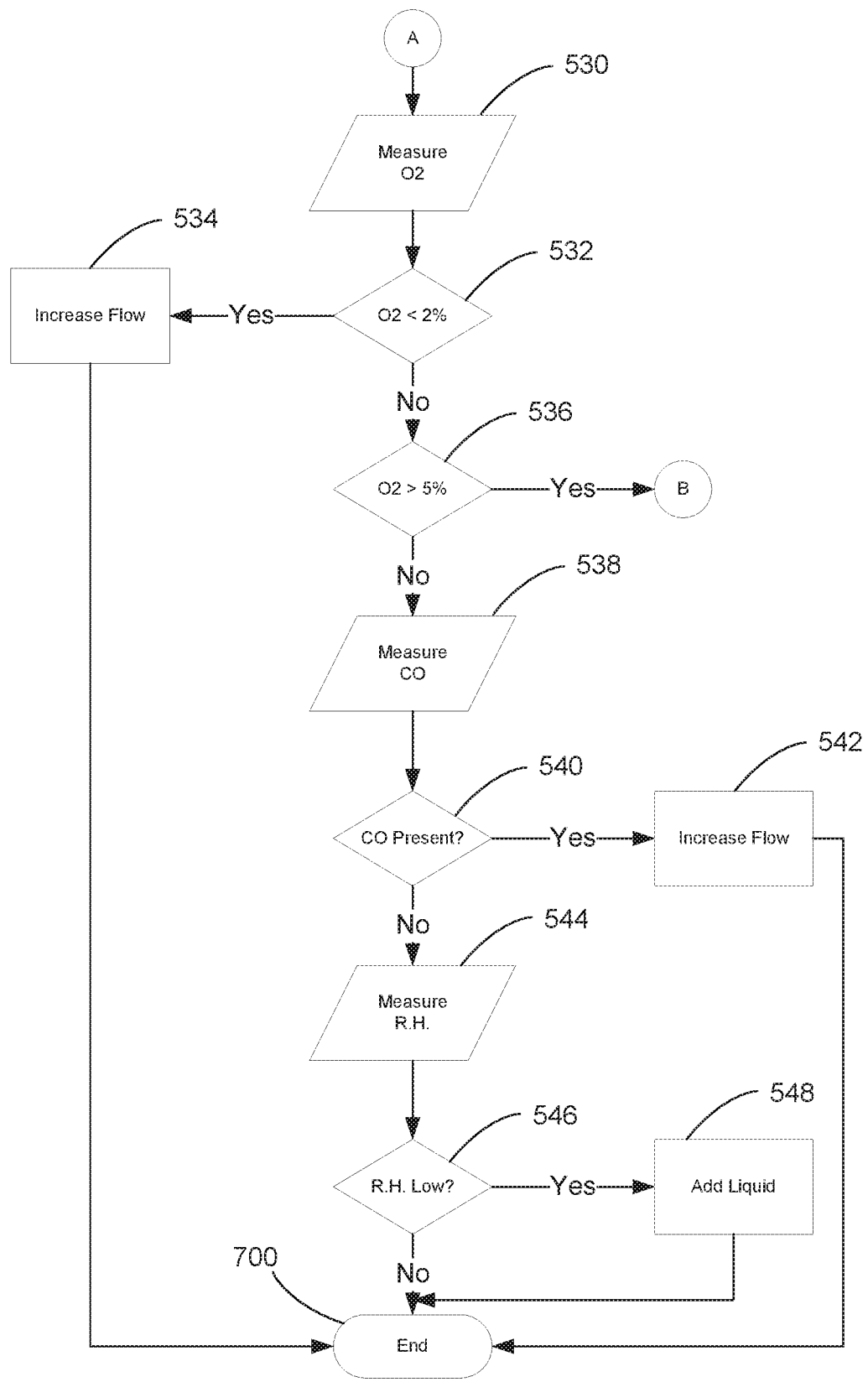

Turning to FIG. 5B, at step 530 the percentage of oxygen in the extracted landfill gas is measured. If the percentage of oxygen is lower than a predetermined oxygen percentage lower limit, for example 2%, then at step 534 the flow of air into the bioreactor is increased. As noted above, the determination of gas constituents may be conducted on specific zones or even specific well heads, by isolating other zones and/or well heads of the bioreactor using isolation valves (e.g. 116) and the flow control valves (e.g. 104). Similarly, increasing the flow of air into the bioreactor may be done on a zone or well head basis by using isolation valves (e.g. 221) and the flow control valves (e.g. 206) to isolate zones or well heads to that ensure only zones or well heads reporting low oxygen get the increased flow. Increasing air flow for a particular well head or zone is accompanied by an increase in the gas extraction rate for that well head or zone. Accordingly, the gas extraction blower is adjusted, by means of the controller, to produce appropriate suction in light of the increased air flow into the corresponding zone or well head, and the flow control valves (e.g. 104) at the desired well heads are also increased. At step 536, if the oxygen percentage in the extracted landfill gas is greater than an oxygen percentage upper limit, for example 5%, then control transfers to step 560 of FIG. 5C.

Figure 5C:
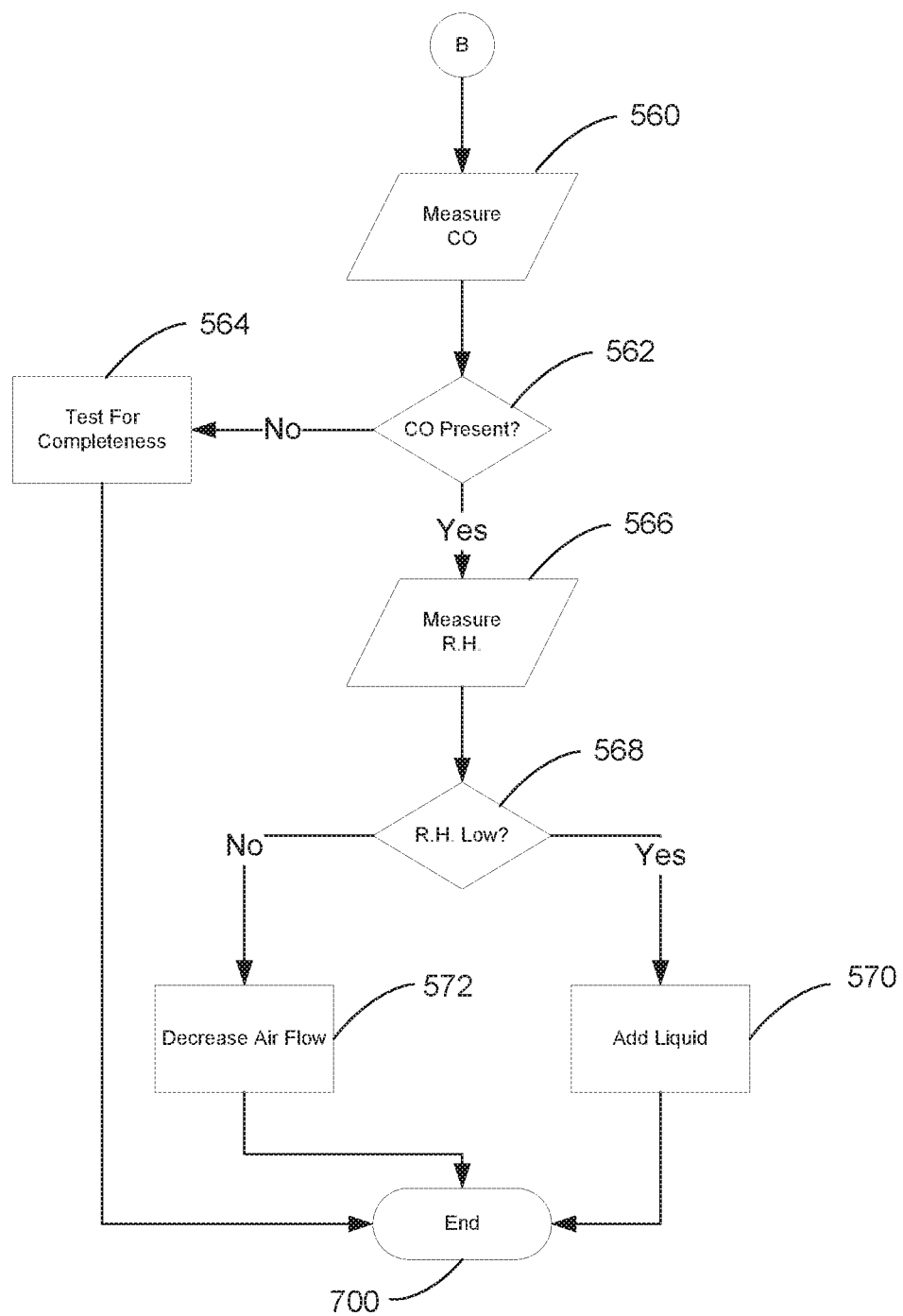
Figure 5D:
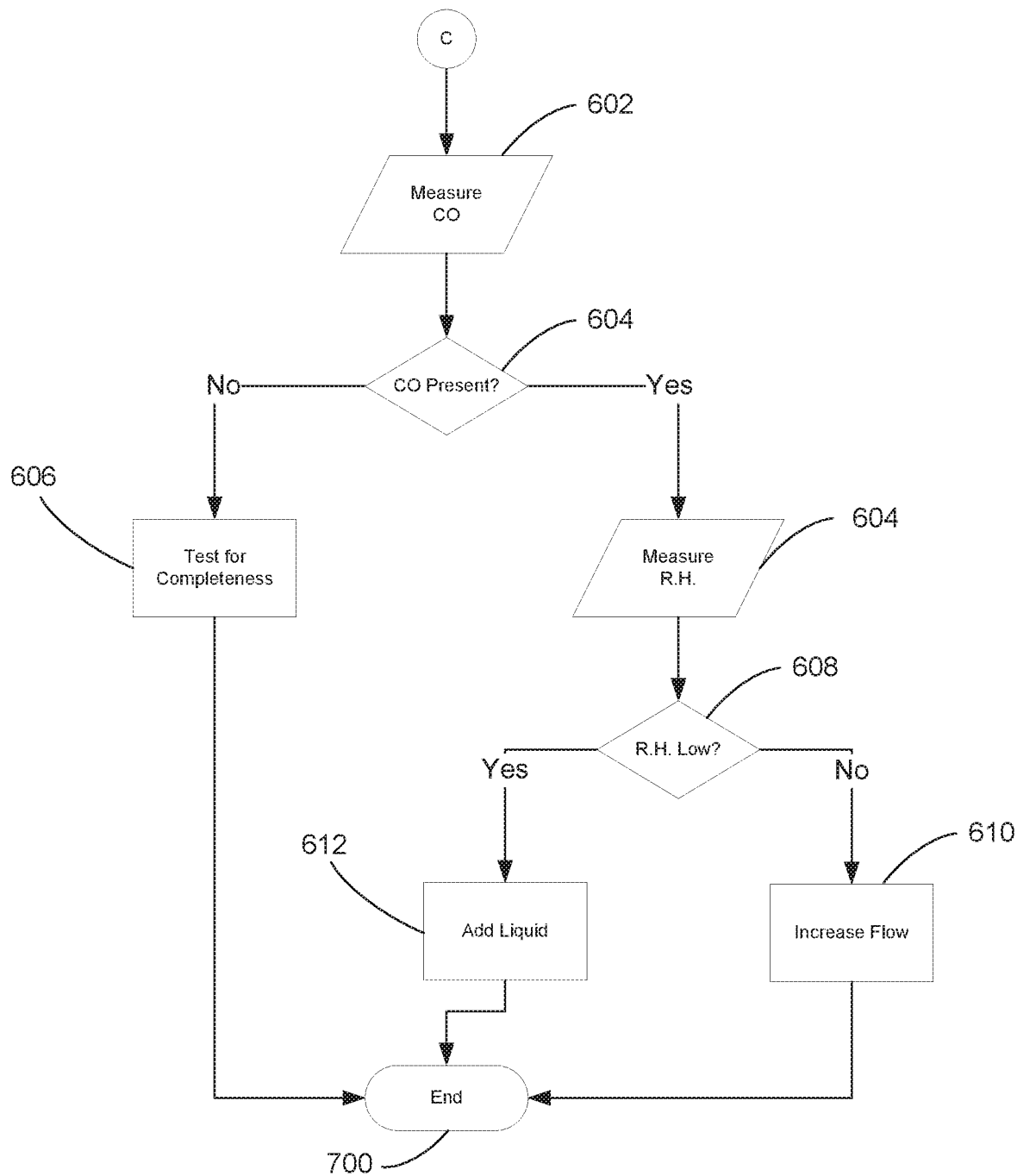

Turning to FIG. 5C, at step 560 the concentration of carbon monoxide (CO) in the extracted landfill gas is measured. At 562, the concentration of CO is checked to see if it is there is CO present in the landfill gas. If there is no CO present, then at step 564 a test for completeness is performed by sampling the waste in the zone to determine if the organic material is stabilized. If there is CO present, then at 566 the relative humidity is measured. Next, the relative humidity is used in the moisture balance calculation. It is desired that the moisture content be maintained in a range that is between the wilting point and the field capacity of the stored waste. If the relative humidity, checked at step 568, is below a lower limit it indicates that there is insufficient moisture in the landfill, then at 570 more liquid is added to the bioreactor to rectify the situation. Conversely, if the humidity is above an upper limit, corresponding to an over removal of moisture, then at 572 the air flow is decreased. The process ends at 700, to be restarted again at 502 of FIG. 5A at the next iteration thereof.

Turning back to FIG. 5B, and particularly at step 538. The percentage oxygen is in the range of 2% to 5%. At 538 the presence of CO in the extracted landfill gas is checked. At 540 if CO is present then control goes to step 542 where the air flow is increased. Conversely, if CO is not present in the extracted landfill gas, then relative humidity is measured at step 544 and checked at 546. If the relative humidity is high, then more liquid is added at step 548. The process ends at step 700.

Figure 5E:
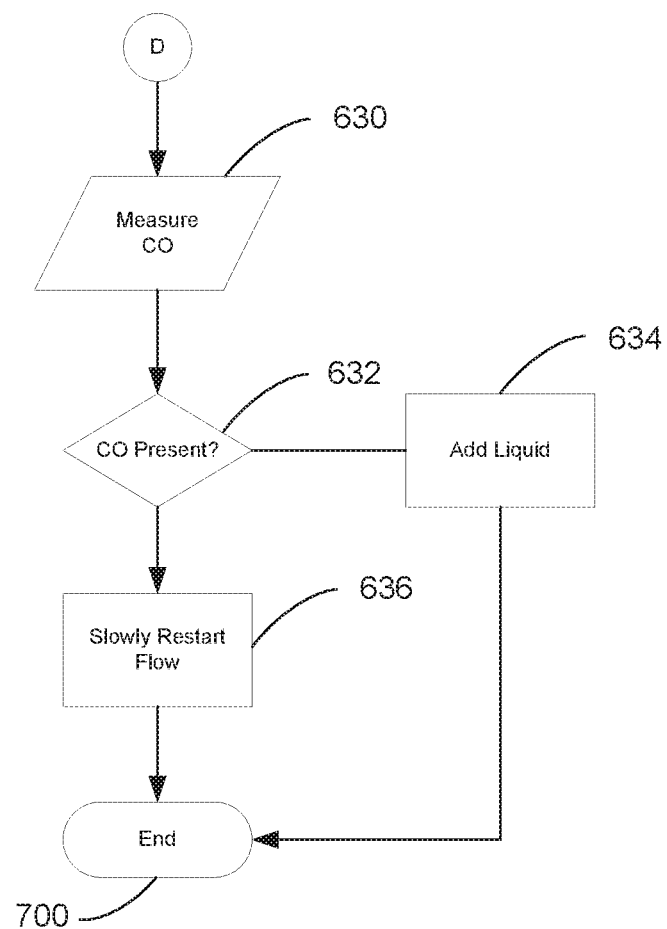

Turning back to FIG. 5A, and particularly to step 508 where the measured temperature is then checked to see if it higher than a predetermined upper limit such as 70 degrees Celsius. If that is the case, control goes to step 630 of FIG. 5E, where control logic is carried out to handle cases where the bioreactor temperature is above (higher than) the predetermined upper limit. Turning now to FIG. 5E. At step 630 the presence of CO as a gas constituent is measured. At 632 if CO is detected, then control proceeds to step 634 where more liquid is injected into the bioreactor. Conversely, if no CO is detected then flow of air is stopped and gas extraction is continued at a low rate. If temperatures decrease air flow and gas extraction are slowly restarted at 636.

Turning back to FIG. 5A, and particularly to step 510. At this point, the measured bioreactor temperature is between the predetermined lower limit and the predetermined upper limit. At 510 the percentage of oxygen in the extracted landfill gas is measured. At step 512 if oxygen is determined to be less than a predetermined lower oxygen percentage limit, such as 2%, then at 514, the flow of air into the bioreactor is increased, along with the rate of gas extraction. At step 516 if oxygen is over 5% then control transfers to step 602 of FIG. 5D. At 602, CO is measured. At 602 if CO is not present, then a test for completeness 606 is carried out by verifying the presence of methane and carbon dioxide in the extracted landfill gas and sampling the waste and determining the extent of stabilization. At 602 if CO is present, then at 604 the relative humidity is measured. At 608, if the relative humidity is low, then at 612 liquid is added to the bioreactor. Otherwise, if relative humidity is not low, then the air injection and gas extraction rates are increased at 610.

Turning back to FIG. 5A, if Oxygen is between 2% and 5%, then control goes to step 518 where CO is measured. At 520, if CO is detected then the air injection and gas extraction rates are increased at 522. Otherwise, control ends at step 700, and the process is restarted.

The above-described embodiments are intended to be examples of the present invention and alterations and modifications may be effected thereto, by those of skill in the art, without departing from the scope of the invention, which is defined solely by the claims appended hereto.

What is claimed is:

1. A method of monitoring or controlling an aerobic landfill bioreactor, the method comprising:
    extracting a landfill gas from the landfill bioreactor via at least one gas extraction well head;
    measuring a temperature of the extracted landfill gas in the at least one gas extraction well head;
    measuring a relative humidity of the extracted landfill gas;
    measuring a concentration of at least one gas constituent of the extracted landfill gas;
    determining at least one operating condition of the aerobic landfill bioreactor based on the measured temperature, relative humidity, and at least one gas constituent;
    controlling fluid being injected into or drawn out of the aerobic landfill bioreactor based on the at least one operating condition;
    measuring initial leachate condition to determine the initial amount of moisture in the aerobic landfill bioreactor;
    measuring liquid infiltrating into the aerobic landfill bioreactor; and
    conducting a water balance computation to determine an upper humidity limit and a lower humidity limit.

2. The method of claim 1, wherein the lower relative humidity limit indicates that insufficient moisture is being drawn from the bioreactor thus increasing moisture content; and wherein the upper relative humidity limit indicates that too much moisture is being drawn from the bioreactor thus decreasing its moisture content.

3. The method of claim 2, wherein the fluid is at least one of: liquid and air being injected into the aerobic landfill bioreactor based on the at least one operating condition.

4. The method of claim 3, wherein the aerobic landfill bioreactor is comprised of a plurality of zones, and the method further comprises configuring a header system to isolate zones such that the controlling at least one of liquid and water is done for only zones having the operating condition.

5. The method of claim 2, wherein the at least one constituent comprises oxygen.

6. The method of claim 2, wherein the at least one gas constituent comprises carbon monoxide.

7. The method of claim 2, wherein the at least one gas constituent comprises oxygen and carbon monoxide.

8. The method of claim 5, further comprising: if the measured temperature is greater than a lower temperature limit and less than an upper temperature limit; and if the oxygen in the extracted landfill gas is less than a lower oxygen percentage limit; then increasing a flow of air through the aerobic landfill bioreactor.

9. The method of claim 7, further comprising: if the measured temperature is greater than a lower temperature limit and less than an upper temperature limit; if the oxygen in the extracted landfill gas is greater than a lower oxygen percentage limit and less than an upper oxygen percentage limit; and if the carbon monoxide is present in the extracted landfill; then increasing a flow of air into the aerobic landfill bioreactor.

10. The method of claim 5, further comprising: if the measured temperature is less than a lower temperature limit; and if the oxygen in the extracted landfill gas is less than a lower oxygen percentage limit; then increasing a flow of air into the aerobic landfill bioreactor.

11. The method of claim 7, further comprising: if the measured temperature is less than a lower temperature limit; if the oxygen in the extracted landfill gas is greater than a lower oxygen percentage limit and less than an upper oxygen percentage limit; and if the carbon monoxide is present in the extracted landfill gas; then increasing a flow of air into the aerobic landfill bioreactor.

12. The method of claim 7, further comprising: if the measured temperature is less than a lower temperature limit; if the oxygen percentage in the extracted landfill gas is greater than a lower oxygen percentage limit and less than a higher oxygen percentage limit; if the carbon monoxide is not present in the extracted landfill gas; and if the measured relative humidity is greater than the upper relative humidity limit; then adding liquid to the aerobic landfill bioreactor.

13. The method of claim 7, further comprising: if the measured temperature is less than a lower temperature limit; if the oxygen percentage in the extracted landfill gas is greater than an upper oxygen percentage limit; and if carbon monoxide is not present in the extracted landfill gas; then performing a test for completeness.

14. The method of claim 7, further comprising: if the measured temperature is less than a lower temperature limit; if the oxygen percentage in the landfill gas is greater than an upper oxygen percentage limit; and if the carbon monoxide is present in the extracted landfill gas; and if the measured relative humidity is less than the lower relative humidity limit; then adding liquid to the aerobic landfill bioreactor.

15. The method of claim 7, further comprising: if the measured temperature is less than a lower temperature limit; if the oxygen in the extracted landfill gas is greater than an upper oxygen percentage limit; if the carbon monoxide is present in the extracted landfill gas; and if the measured relative humidity is greater than the upper relative humidity limit; then decreasing the flow of air into the aerobic landfill bioreactor.

16. The method of claim 7, further comprising: if the measured temperature is greater than a lower temperature limit and less than an upper temperature limit; if the oxygen in the extracted landfill gas is greater than an upper oxygen percentage limit; if the carbon monoxide is present in the extracted landfill gas; and if the measured relative humidity is less than the lower relative humidity limit; then adding liquid to the aerobic landfill bioreactor.

17. The method of claim 7, further comprising: if the measured temperature is greater than a lower temperature limit and less than an upper temperature limit; if the oxygen in the extracted landfill gas is greater than an upper oxygen percentage limit; and if the carbon monoxide is not present in the extracted landfill gas; then performing a test for completeness.

18. The method of claim 7, further comprising: if the measured temperature is greater than a lower temperature limit and less than an upper temperature limit; if the oxygen in the extracted landfill gas is greater than an upper oxygen percentage limit; if the carbon monoxide is present in the extracted landfill gas; and if the measured relative humidity is greater than the upper relative humidity limit; then increasing the flow of air into the aerobic landfill bioreactor.

19. The method of claim 6, further comprising: if the measured temperature is greater than an upper temperature limit; and if the carbon monoxide is present in the extracted landfill gas; then adding liquid to the aerobic landfill bioreactor.

20. The method of claim 6, further comprising: if the measured temperature is greater than an upper temperature limit; and if the carbon monoxide is not present in the extracted landfill gas; then the system is stopped and the air flow into the aerobic landfill bioreactor is slowly restarted.

\* \* \* \* \*